(12) United States Patent
Wilhelm et al.

(10) Patent No.: US 12,721,999 B2
(45) Date of Patent: Sep. 1, 2026

(54) LEAD FOR A MEDICAL DEVICE

(71) Applicant: Heraeus Medevio GmbH & Co. KG, Hanau (DE)

(72) Inventors: Leoni Wilhelm, Hanau (DE); Mark A. Hjelle, Fridley, MN (US); Michael Seffren, Fridley, MN (US); Andreas Reisinger, Hanau (DE)

(73) Assignee: Heraeus Medevio GmbH & Co. KG, Hanau (DE)

( * ) Notice: Subject to any disclaimer, the term of this patent is extended or adjusted under 35 U.S.C. 154(b) by 202 days.

(21) Appl. No.: 18/613,841

(22) Filed: Mar. 22, 2024

(65) Prior Publication Data

US 2024/0325729 A1 Oct. 3, 2024

Related U.S. Application Data

(60) Provisional application No. 63/455,779, filed on Mar. 30, 2023.

(51) Int. Cl.
*A61N 1/05* (2006.01)
*A61N 1/36* (2006.01)

(52) U.S. Cl.
CPC ............. *A61N 1/05* (2013.01); *A61N 1/3605* (2013.01)

(58) Field of Classification Search
CPC ......... A61N 1/05; A61N 1/3605; A61N 1/056
See application file for complete search history.

(56) References Cited

U.S. PATENT DOCUMENTS 4,328,812 A 5/1982 Ufford et al.
4,484,586 A 11/1984 Mcmickle et al.
6,018,683 A * 1/2000 Verness ................ A61N 1/0573 607/122
7,239,922 B1 * 7/2007 Boogaard ............. A61N 1/056 607/116
7,761,170 B2 7/2010 Kaplan et al.
8,868,213 B2 10/2014 Shan et al.
9,014,822 B2 4/2015 Ollivier et al.
(Continued)

FOREIGN PATENT DOCUMENTS

CN 104364855 A 2/2015
EP 2682151 A1 1/2014
(Continued)

*Primary Examiner* — Carl H Layno
*Assistant Examiner* — Maria Catherine Anthony
(74) *Attorney, Agent, or Firm* — Dicke, Billig & Czaja, PLLC

(57) ABSTRACT

One aspect refers to a lead for a medical device, including a cable comprising an outer insulation having at least one first opening near a distal end of the cable and an inner lumen. The inner lumen is arranged coaxially to the outer insulation. At least one conducting channel is arranged between the outer insulation and the inner lumen. The at least one conducting channel is formed by at least one insulated conductor. The insulation layer comprises a second opening, which is aligned with the at least one first opening. At least one ring electrode surrounds the cable at a position of the at least one aligned first and second opening of the cable. The at least one ring electrode is selectively connected to the conductor of the at least one insulated conductor via a bendable bridging element extending through the at least one aligned first and second opening.

17 Claims, 7 Drawing Sheets

(56) References Cited

U.S. PATENT DOCUMENTS

| | | | | |
|---|---|---|---|---|
| 9,067,058 | B2 | 6/2015 | Ollivier et al. | |
| 9,216,283 | B2 | 12/2015 | Ollivier et al. | |
| 9,248,271 | B2 | 2/2016 | Regnier et al. | |
| 9,333,335 | B2 | 5/2016 | Ollivier et al. | |
| 9,907,951 | B2 | 3/2018 | Régnier et al. | |
| 10,071,238 | B2 | 9/2018 | Ollivier et al. | |
| 10,463,848 | B2 | 11/2019 | Ollivier et al. | |
| 10,675,459 | B2 | 6/2020 | Regnier et al. | |
| 11,103,694 | B2 | 8/2021 | Ollivier et al. | |
| 11,426,575 | B2 | 8/2022 | Julien et al. | |
| 2001/0025192 | A1 | 9/2001 | Gerber et al. | |
| 2002/0099430 | A1* | 7/2002 | Verness | A61N 1/056 607/122 |
| 2009/0054947 | A1 | 2/2009 | Bourn et al. | |
| 2009/0134134 | A1 | 5/2009 | Wessman | |
| 2009/0222074 | A1 | 9/2009 | Zarembo et al. | |
| 2009/0326626 | A1 | 12/2009 | Swoyer | |
| 2011/0160830 | A1* | 6/2011 | Morris | A61N 1/056 607/116 |
| 2012/0271386 | A1 | 10/2012 | Li et al. | |
| 2013/0096647 | A1 | 4/2013 | Amara et al. | |
| 2013/0338745 | A1 | 12/2013 | Ollivier et al. | |
| 2014/0012355 | A1 | 1/2014 | Ollivier et al. | |
| 2014/0107456 | A1 | 4/2014 | Régnier et al. | |
| 2015/0099958 | A1 | 4/2015 | Shan et al. | |
| 2016/0235967 | A1 | 8/2016 | Shan et al. | |
| 2020/0009370 | A1 | 1/2020 | Julien et al. | |
| 2020/0061367 | A1 | 2/2020 | Régnier et al. | |
| 2022/0134091 | A1 | 5/2022 | Jung et al. | |

FOREIGN PATENT DOCUMENTS

| | | | |
|---|---|---|---|
| EP | 2732848 | A1 | 5/2014 |
| EP | 2810686 | A1 | 12/2014 |
| EP | 2842136 | B1 | 6/2017 |
| EP | 3591763 | A1 | 1/2020 |
| FR | 2989817 | | 10/2013 |
| JP | 2013056150 | A | 3/2013 |
| WO | 2006047145 | A1 | 5/2006 |

* cited by examiner 10
6
11
7
2
1
4
3
13
14
13
11
2
7
6
4

LEAD FOR A MEDICAL DEVICE

CROSS-REFERENCE TO RELATED APPLICATIONS

This application claims the benefit of and priority to U.S. application Ser. No. 63/455,779, having a filing date of Mar. 30, 2023, which is hereby incorporated by reference.

TECHNICAL FIELD

One aspect relates to a lead, and to a process for preparing the lead. The lead is useful for a medical device, and for a temporary test trial lead. However, the lead may also be used in other technical fields.

BACKGROUND

Leads, and especially multipolar leads, for medical devices are usually very complex to manufacture as their preparation requires many different components which need to be assembled in many steps. Manufacturing is even more complex in case of small sized leads, which are particularly desired in the field of medical devices. The complex design of leads and the manufacturing processes for preparing the same usually lead to high prices for the end product.

The high prices of known leads are particularly problematic, if the leads are intended to be used in medical devices over a comparatively short time, e.g. in a temporary medical test trial set-up. To conduct temporary medical test trials in economically feasible manner, cheaper unipolar leads are therefore chosen for the trials. However, the use of a unipolar lead can limit the success of the test trial, which can ultimately result in less patients receiving the appropriate medical treatment in form of a permanent medical device.

Furthermore, a lead which is designed and manufactured by using a high number of single components can have a lower reliability due to more possible failure modes of the single pieces. Thus, a lower reliability can lead to a higher risk of failure for the lead, which in turn can have significant consequences, e.g. for the health of a patient when the lead is used in a medical device.

In view of the foregoing, it is desired to provide a lead which has a comparatively simple design and/or which contains comparatively little components while still having a good reliability. The lead shall be obtainable by a simple and efficient manufacturing process.

Therefore, the present embodiment is directed to the provision of an improved, or at least alternative, lead, which is useful for a medical device.

SUMMARY

One aspect of the present embodiment refers to a lead for a medical device including:

a cable including an outer insulation having at least one first opening near a distal end of the cable;

an inner lumen, wherein the inner lumen is arranged coaxially to the outer insulation and extends in a longitudinal direction from a proximal end to the distal end of the cable;

at least one conducting channel, wherein the at least one conducting channel is arranged between the outer insulation and the inner lumen of the cable, wherein the at least one conducting channel is formed by at least one insulated conductor including a conductor and an insulation layer, and wherein the insulation layer of the at least one insulated conductor comprises a second opening, which is aligned with the at least one first opening;

at least one ring electrode, wherein the at least one ring electrode surrounds the cable at a position of the at least one aligned first and second opening of the cable, and wherein the at least one ring electrode is selectively connected to the conductor of the at least one insulated conductor via a reversible bendable, bridging element extending through the at least one aligned first and second opening.

The inventors found that by designing and manufacturing a lead according to the present embodiment, a lead is available which is simple, small in size and can be prepared in an efficient and reliable way. In particular, the inventor's findings resulted in a lead having its complete lead body on the cable or coil which allows for a particularly high miniaturization. The inventive lead has comparatively little components, and especially provides a reliable and good electrical contact between conductor and ring electrode. The design of the inventive lead also allows for attaching the ring electrode at any desired position of the cable.

The second opening in the insulation of the insulated conductor is limited in size to allow for a good connectivity to the ring electrode, while at the same time maintaining the insulation towards the insulated conductor(s) of other conducting channels. Thereby, the dielectric strength/resistance against electrical short circuits towards insulated conductor (s) of other conducting channels within the lead is increased. The inventive lead can be produced in a very efficient and cheap manner so that the inventive lead may also be used for temporary applications (e.g. temporary medical test trials), where the use of other known leads, in particular multipolar leads, would not be attractive from an economic standpoint.

Another aspect of the present embodiment is a process for preparing a lead according to the present embodiment. The process comprises the steps of:

a) providing a cable including an outer insulation, an inner lumen, wherein the inner lumen is arranged coaxially to the outer insulation and extends in a longitudinal direction from a proximal end to a distal end of the cable, at least one conducting channel, wherein the at least one conducting channel is arranged between the outer insulation and the inner lumen of the cable, wherein the at least one conducting channel is formed by at least one insulated conductor including a conductor and an insulation layer;

b) providing at least one ring electrode;

c) providing at least one bendable bridging element;

d) removing parts of the outer insulation near the distal end of the cable to create at least one first opening;

e) removing parts of the insulation layer of the at least one insulated conductor beneath the at least one first opening to create at least one second opening, wherein the at least one second opening is aligned with the at least one first opening near the distal end of the cable;

f) positioning the at least one bridging element in the aligned first and second opening so that the bridging element is in electrical contact with the conductor;

g) attaching the bridging element to the conductor;

h) positioning the at least one ring electrode around the cable obtained in step g) at the position of the at least one aligned first and second opening;

i) attaching the at least one ring electrode to the bridging element thereby connecting the at least one ring electrode to the conductor.

The inventors found that the lead according to the present embodiment can be prepared in an efficient and simple manner. The cable or coil on which the lead is based can be produced as a long ("endless") cable on a spool which is shortened to the desired length of the lead. The openings are introduced into the cable, which allow for connecting the ring electrode to the conductors of the conducting channels via the bridging element in an efficient procedure and thus providing a robust and reliable electrical connection between the conductor(s) and the ring electrode. In particular, the process allows reliable electrical contact to be formed between the conductor(s) and the ring electrode despite any process variations, such as irregular thickness of the outer insulation of the cable.

It should be understood that for the purposes of the present embodiment, the following terms have the following meanings:

A "lead" in the meaning of the present embodiment is a lead including at least one conducting channel and at least one ring electrode near the distal end of the cable. A "bipolar" lead in the meaning of the present embodiment is a lead including two conducting channels and two ring electrodes near the distal end of the cable. A "multipolar" lead is a lead including at least three conducting channels and at least three ring electrodes near the distal end of the cable. In general, the polarity of the lead is determined by the number of conducting channels of the lead. Since each conducting channel is selectively connected to at least one ring electrode near the distal end of the cable, the number of conducting channels also determines the minimum number of ring electrodes near the distal end of the cable. Thus, a multipolar lead including four conducting channels can comprise a minimum of four ring electrodes near the distal end.

"Near the distal end" of the cable means for this embodiment that a position lies within the last 30%, 20%, or 10%, of the length of the cable, and "near the proximal end" means that a position lies within the first 30%, 20%, or 10%, of the length of the cable.

A "first opening" in the meaning of the present embodiment is a hole in the outer insulation near the distal end of the cable, by which a part of the at least one insulated conductor of one conducting channel is exposed.

A "second opening" in the meaning of the present embodiment is a hole in the insulation layer of the at least one insulated conductor of one conducting channel, by which a part of the conductor of the at least one insulated conductor is exposed. The size and shape of the second opening is selected in a way that the part of the insulation layer, which is in contact with the insulation layer of an insulated conductor of another conducting channel, remains intact. In one embodiment, the second opening is located on the top side of the at least one insulated conductor. The "top side" of the at least one insulated conductor is the side of the insulated conductor, which points radially outward, as seen from the center of the cable.

An "inner lumen" in the meaning of the present embodiment is a free space in the center of the lead.

A "conducting channel" in the meaning of this embodiment is a mean to selectively, electrically connect an electrical part (e.g. a ring electrode) near the proximal end of the lead with a ring electrode near the distal end of the lead.

If a second opening of the insulation layer of an insulated conductor is "aligned" with a first opening of the outer insulation, this means that the first and second openings at least partially overlap, and in one embodiment, that the second opening fully overlaps with the first opening.

Where an indefinite or definite article is used when referring to a singular noun, e.g., "a", "an" or "the", this includes a plural of that noun unless anything else is specifically stated. Where the term "comprising" is used in the present description and claims, it does not exclude other elements.

For the purposes of the present embodiment, the terms "essentially consisting of" and "consisting of" are considered to be a preferred embodiments of the term "comprising". If hereinafter a group is defined to comprise at least a certain number of embodiments, this is also to be understood to disclose a group, which essentially consists of only of these embodiments, or consists of only of these embodiments.

Terms like "obtainable" or "definable" and "obtained" or "defined" are used interchangeably. This, for example, means that, unless the context clearly dictates otherwise, the term "obtained" does not mean to indicate that, for example, an embodiment must be obtained by, for example, the sequence of steps following the term "obtained" though such a limited understanding is always included by the terms "obtained" or "defined" as one embodiment. Whenever the terms "including" or "having" are used, these terms are meant to be equivalent to "comprising" as defined hereinabove.

The term "essentially" is to be understood in such a way that under real conditions and manufacturing techniques, a mathematically exact interpretation of terms such as "superimposition", "perpendicular", "diameter" or "parallelism" can never be given exactly, but only within certain manufacturing tolerances. For example, "substantially perpendicular axes" include an angle of 80 degrees to 100 degrees with respect to each other, and "substantially equal volumes" include a variation of up to 5% by volume. For example, a "substantially plastic device" includes a plastic content of ≥95 to ≤100 weight %. For example, a "substantially complete filling of a volume B" comprises a filling of ≥95 to ≤100 volume % of the total volume of B.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

The following schematic drawings show aspects of the invention for improving the understanding of the embodiment in connection with some exemplary illustrations, wherein

FIG. 1 exemplarily shows a cable (10) in a radial cross section (upper) and in a longitudinal cross section (lower, only a section is shown). Each of the six conducting channels can be electrically connected to a separate ring electrode, making the cable (10) suitable for the manufacturing of a lead with six ring electrodes. The cable (10) comprises an outer insulation (1) having a first opening (2). The cable further comprises an inner lumen (3) formed by an inner polymer tube (4) and six conducting channels. One conducting channel (5) is formed by two insulated conductors, wherein each one of the insulated conductors comprises a conductor (6) and an insulation layer (7). The insulation layer has a second opening (8). The second opening (8) is positioned on the top side of the insulated conductor, and points radially outward towards the outside of the cable. The second opening (8) is aligned with the first opening (2) in the outer insulation (1) of the cable (10).

FIG. 2 shows a schematic drawing of a process for preparing a multipolar lead according to one embodiment. The lead comprises six conducting channels and six ring electrodes near the distal end of the lead.

FIG. 3 shows a schematic drawing of another process for preparing a multipolar lead according to one embodiment. The lead comprises six conducting channels and six ring electrodes near the distal end of the lead.

FIG. 3B also shows the ring electrode (13') in top view (lower right), the ring electrode having an indentation (13'A) in which the stopper element of the leaf spring can engage.

FIG. 4 shows a schematic drawing of another process for preparing a multipolar lead according to one embodiment. The lead comprises six conducting channels and six ring electrodes near the distal end of the lead.

FIG. 5 shows a schematic drawing of another process for preparing a multipolar lead according to one embodiment. The lead comprises six conducting channels and six ring electrodes near the distal end of the lead.

FIG. 5B also shows the ring electrode (13') in top view (lower right), the ring electrode having an indentation (13'A) in which the end of the wire that is radially bent outward from the longitudinal axis of the cable can engage.

FIG. 6 shows a schematic drawing of another process for preparing a multipolar lead according to one embodiment. The lead comprises six conducting channels and six ring electrodes near the distal end of the lead.

FIG. 7 shows a schematic drawing of another process for preparing a multipolar lead according to one embodiment. The lead comprises six conducting channels and six ring electrodes near the distal end of the lead.

DETAILED DESCRIPTION

Figure 1:
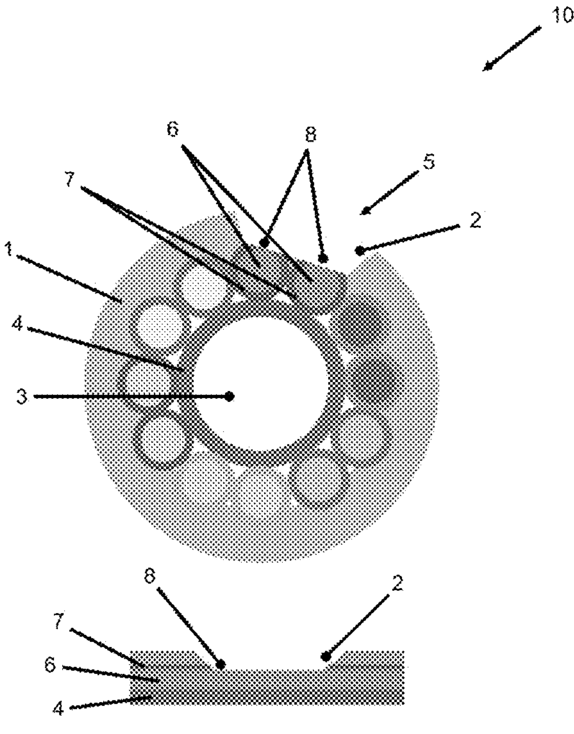
FIG. 1 shows a schematic drawing of a cable for a multipolar lead according to one embodiment, wherein the cable comprises six conducting channels.
Figures 2A, 2B, 2C:
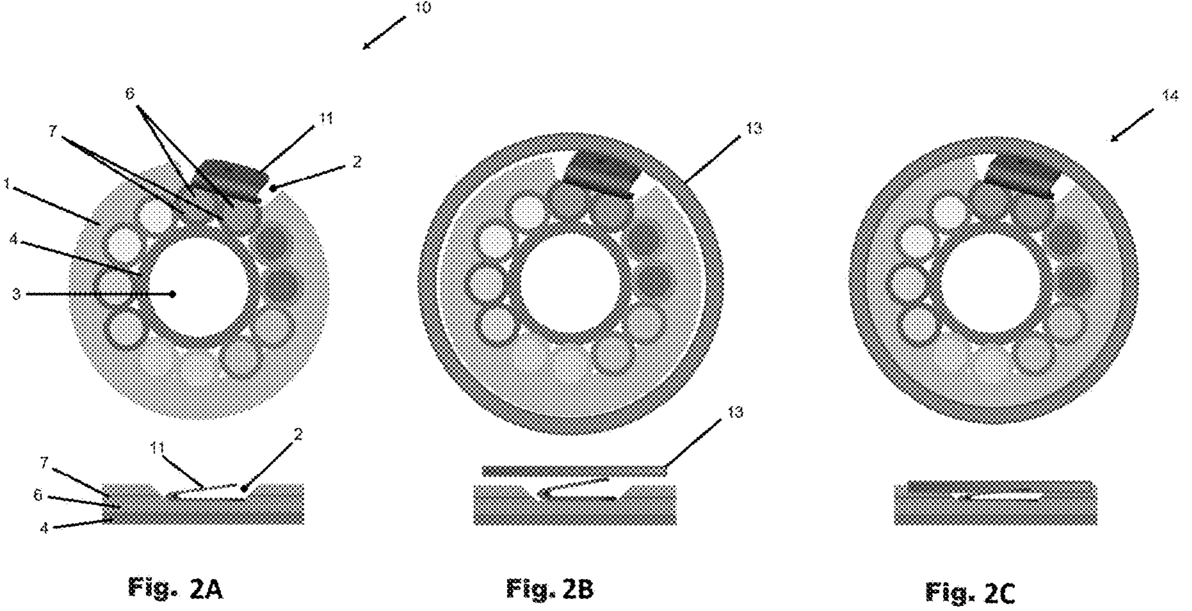
FIG. 2A shows the cable (10) of FIG. 1 in a radial cross section (upper) and in a longitudinal cross section (lower, only a section of the is shown) for the attachment of one of the six ring electrodes. To avoid repetition, reference is made to the explanations of FIG. 1 for the individual features of the cable (10). A bendable bridging element in form of a leaf spring (11) is located in the aligned first opening (2) and second opening (8). The leaf spring (11) is in electrical contact with the conductor (6) of one conducting channel and is thereby aligned so that it can be radially compressed.
FIG. 2B shows a ring electrode (13) positioned over the aligned first opening (2) and second opening (8) of the cable (10) in a radial cross section (upper) and a longitudinal cross section (lower, only a section of the is shown).
FIG. 2C shows a lead (14) according to one embodiment, wherein the ring electrode is electrically connected via the leaf spring to the conductors of the two insulated conductors of one of the six conducting channels through the aligned first and second opening.
Figures 3A, 3B, 3C:
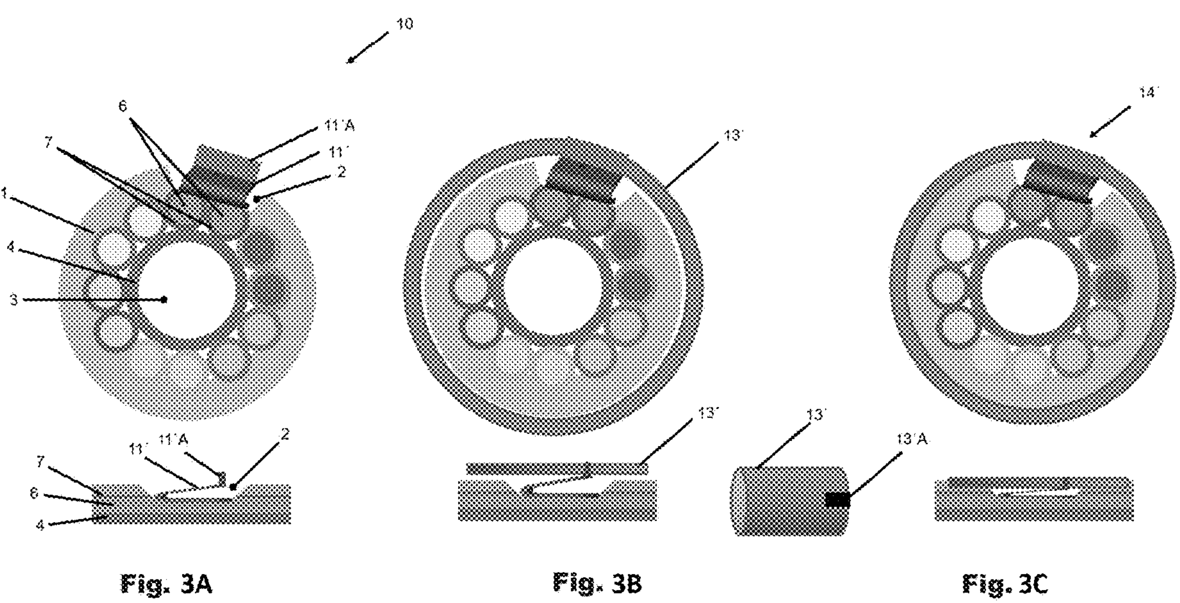
FIG. 3A shows the cable (10) of FIG. 1 in a radial cross section (upper) and in a longitudinal cross section (lower, only a section of the is shown) for the attachment of one of the six ring electrodes. To avoid repetition, reference is made to the explanations of FIG. 1 for the individual features of the cable (10). A bendable bridging element in form of a leaf spring (11') is located in the aligned first opening (2) and second opening (8). On the side facing away from the conductor (6), the leaf spring (11') has a stopper element (11'A). The leaf spring (11') is in electrical contact with the conductor (6) of one conducting channel and is thereby aligned so that it can be radially compressed.
FIG. 3B shows a ring electrode (13') positioned over the aligned first opening (2) and second opening (8) of the cable (10) in a radial cross section (upper) and a longitudinal cross section (lower left, only a section of the is shown).
FIG. 3C shows a lead (14') according to one embodiment, wherein the ring electrode is electrically connected via the leaf spring to the conductors of the two insulated conductors of one of the six conducting channels through the aligned first and second opening. The stopper element of the leaf spring is engaged with the indentation of the ring electrode.
Figures 4A, 4B, 4C:
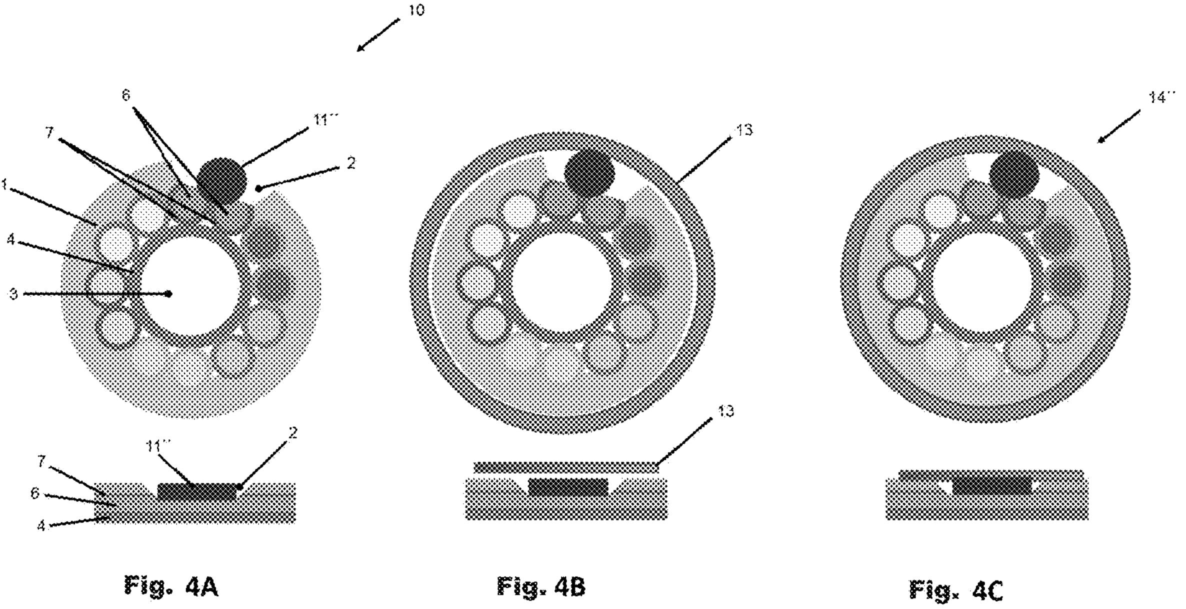
FIG. 4A shows the cable (10) of FIG. 1 in a radial cross section (upper) and in a longitudinal cross section (lower, only a section of the is shown) for the attachment of one of the six ring electrodes. To avoid repetition, reference is made to the explanations of FIG. 1 for the individual features of the cable (10). A bendable bridging element in form of a wire (11") extending essentially parallel to a longitudinal axis of the cable is located in the aligned first opening (2) and second opening (8). The wire (11") is in electrical contact with the conductor (6) of one conducting channel.
FIG. 4B shows a ring electrode (13) positioned over the aligned first opening (2) and second opening (8) of the cable (10) in a radial cross section (upper) and a longitudinal cross section (lower left, only a section of the is shown).
FIG. 4C shows a lead (14") according to one embodiment, wherein the ring electrode is electrically connected via the wire to the conductors of the two insulated conductors of one of the six conducting channels through the aligned first and second opening.
Figures 5A, 5B, 5C:
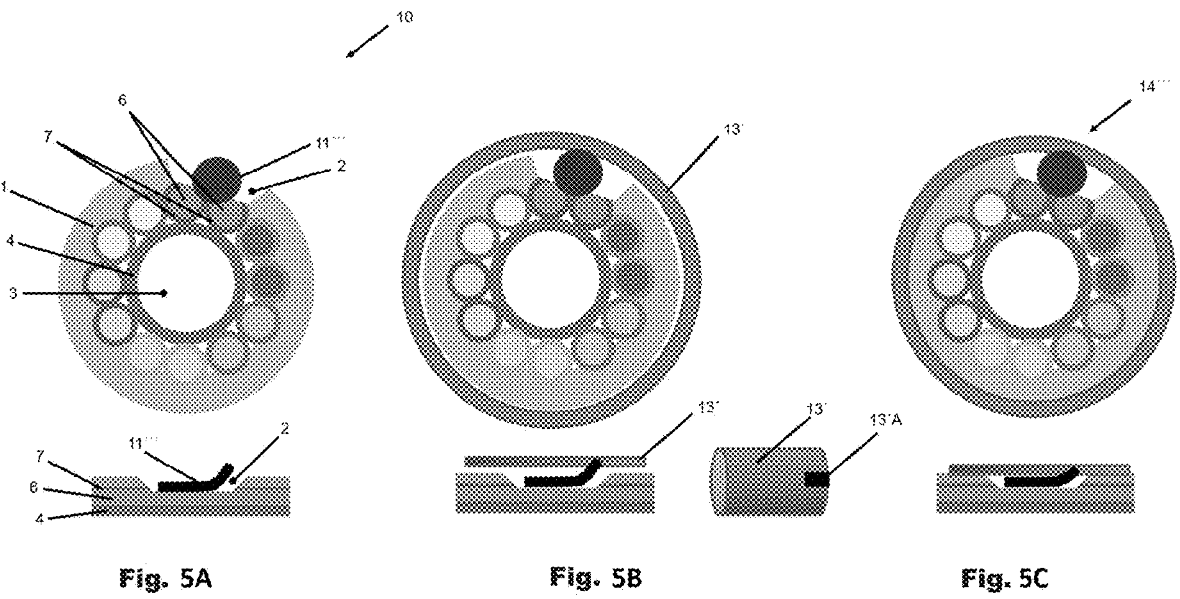
FIG. 5A shows the cable (10) of FIG. 1 in a radial cross section (upper) and in a longitudinal cross section (lower, only a section of the is shown) for the attachment of one of the six ring electrodes. To avoid repetition, reference is made to the explanations of FIG. 1 for the individual features of the cable (10). A bendable bridging element in form of a wire (11'") extending essentially parallel to a longitudinal axis of the cable is located in the aligned first opening (2) and second opening (8). One end of the wire (11'") is bent slightly radially outward from the longitudinal axis of the cable. This can facilitate the formation of an electrical contact with a ring electrode. The wire (11'") is in electrical contact with the conductor (6) of one conducting channel.
FIG. 5B shows a ring electrode (13') positioned over the aligned first opening (2) and second opening (8) of the cable (10) in a radial cross section (upper) and a longitudinal cross section (lower left, only a section of the is shown).
FIG. 5C shows a lead (14'") according to one embodiment, wherein the ring electrode is electrically connected via the wire to the conductors of the two insulated conductors of one of the six conducting channels through the aligned first and second opening. The end of the wire that is bent radially outward from the longitudinal axis of the cable is engaged with the indentation of the ring electrode.
Figures 6A, 6B, 6C:
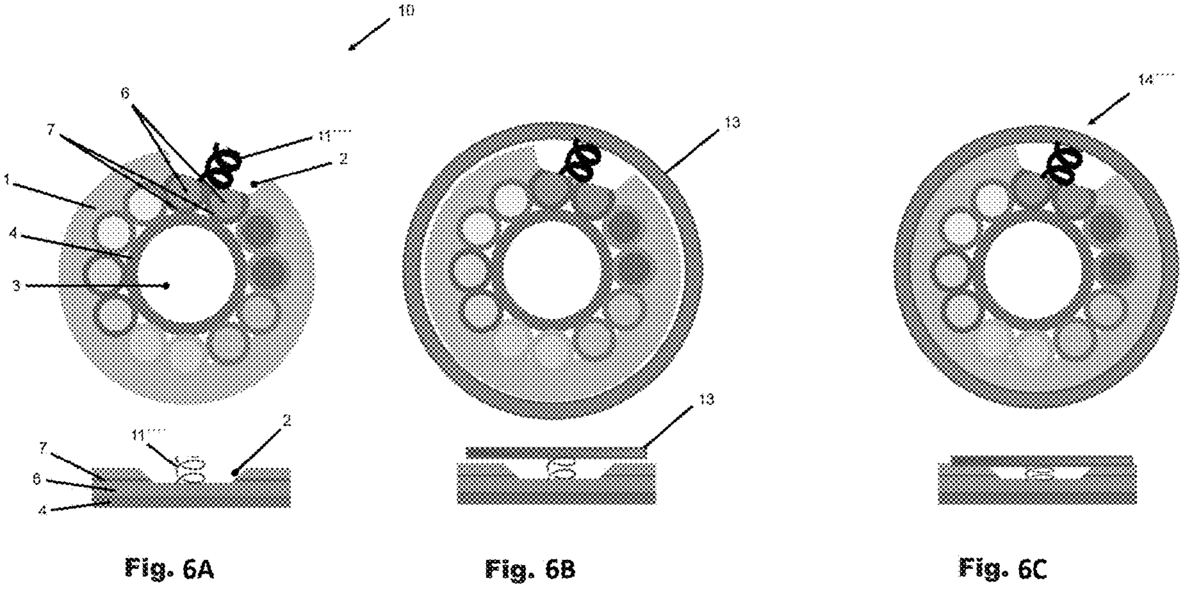
FIG. 6A shows the cable (10) of FIG. 1 in a radial cross section (upper) and in a longitudinal cross section (lower, only a section of the is shown) for the attachment of one of the six ring electrodes. To avoid repetition, reference is made to the explanations of FIG. 1 for the individual features of the cable (10). A bendable bridging element in form of a coil spring (11"") is located in the aligned first opening (2) and second opening (8). The coil spring (11"") is in electrical contact with the conductor (6) of one conducting channel and is thereby aligned so that it can be radially compressed.
FIG. 6B shows a ring electrode (13) positioned over the aligned first opening (2) and second opening (8) of the cable (10) in a radial cross section (upper) and a longitudinal cross section (lower, only a section of the is shown).
FIG. 6C shows a lead (14"") according to one embodiment, wherein the ring electrode is electrically connected via the coil spring to the conductors of the two insulated conductors of one of the six conducting channels through the aligned first and second opening.
Figures 7A, 7B, 7C:
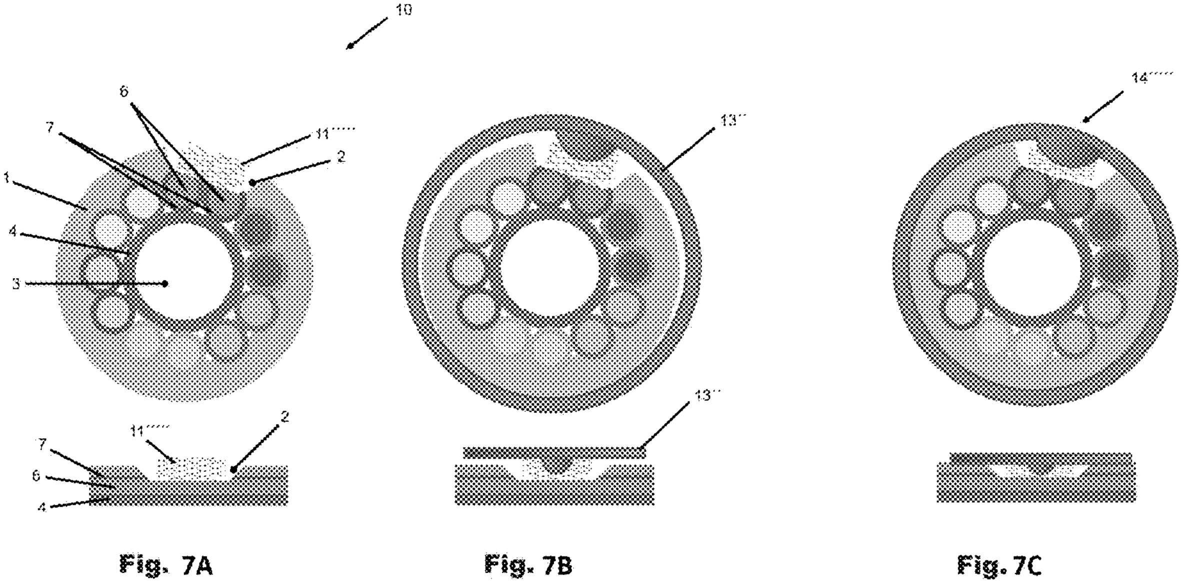
FIG. 7A shows the cable (10) of FIG. 1 in a radial cross section (upper) and in a longitudinal cross section (lower, only a section of the is shown) for the attachment of one of the six ring electrodes. To avoid repetition, reference is made to the explanations of FIG. 1 for the individual features of the cable (10). A bendable bridging element in form of a mesh (11""") is located in the aligned first opening (2) and second opening (8). The mesh (11""") is in electrical contact with the conductor (6) of one conducting channel.
FIG. 7B shows a ring electrode (13") positioned over the aligned first opening (2) and second opening (8) of the cable (10) in a radial cross section (upper) and a longitudinal cross section (lower, only a section of the is shown). The ring electrode comprises a protrusion in the form of an electrode cup which extends radially inwards in the direction of the cable to facilitate the formation of electrical contact between the mesh and the ring electrode in the final lead.
FIG. 7C shows a lead (14""") according to one embodiment, wherein the ring electrode is electrically connected via the mesh to the conductors of the two insulated conductors of one of the six conducting channels through the aligned first and second opening. The protrusion of the ring electrode extends in sections into the first opening of the outer insolation.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

The Lead

One aspect of the present embodiment refers to a lead, a bi- or multipolar lead, for a medical device. The lead for a medical device comprises an outer insulation having at least one first opening near a distal end of the cable, an inner lumen, wherein the inner lumen is arranged coaxially to the outer insulation and extends in a longitudinal direction from a proximal end to the distal end of the cable, at least one conducting channel, wherein the at least one conducting channel is arranged between the outer insulation and the inner lumen of the cable, wherein the at least one conducting channel is formed by at least one insulated conductor including a conductor and an insulation layer, and wherein the insulation layer of the at least one insulated conductor comprises a second opening, which is aligned with the at least one first opening, at least one ring electrode, wherein the at least one ring electrode surrounds the cable at a position of the at least one aligned first and second opening of the cable, and wherein the at least one ring electrode is selectively connected, especially electrically connected, to the conductor of the at least one insulated conductor via a reversible bendable, bridging element extending through the at least one aligned first and second opening.

The lead of one embodiment comprises a cable. The cable has a proximal end and a distal end. The length the cable can be selected by the skilled person in view of the application of the inventive lead and taking into account the present specification. For example, the cable can have a length in the range of 50 to 5000 mm, 100 to 2000 mm, or 200 to 1000 mm. In an exemplary embodiment, the cable has a length of about 500 mm.

The cable comprises an outer insulation. In one embodiment, the outer insulation has an outer diameter in the range of 200 to 5000 μm, 300 to 3000 μm, or 500 to 1500 μm. In an exemplary embodiment, the outer diameter of the outer insulation is about 700 μm. It is to be understood that the outer diameter of the outer insulation of the cable also corresponds to the outer diameter of the cable. The outer insulation has a wall thickness in the range of 2 to 300 μm, 5 to 150 μm, or 20 to 100 μm. According to one embodiment, the outer insulation has an outer diameter in the range of 300 to 3000 μm, or 500 to 1500 μm, and a wall thickness in the range of 5 to 150 μm, or 20 to 100 μm. In an exemplary embodiment, the wall thickness is about 60 μm.

The outer insulation in one embodiment comprises a polymer selected from the group of silicones, polyolefins (e.g. polyethylene), polyurethanes, polyimides, polyamides, polyaryletherketone (e.g. polyether ether ketone), fluorinated polymers (e.g. selected from the group of ethylene tetrafluorethylene, polytetrafluorethylene, perfluoroalkoxy alkanes, polyvinylidene fluorides, fluorinated ethylene propylene, and mixtures thereof), and mixtures thereof. According to one embodiment, the outer insulation comprises a polymer selected from the group of silicones, polyolefins (e.g. polyethylene), polyurethanes, polyimides, polyamides, polyaryletherketone (e.g. polyether ether ketone), fluorinated polymers (e.g. selected from the group of ethylene tetrafluorethylene, polytetrafluorethylene, perfluoroalkoxy alkanes, polyvinylidene fluorides, fluorinated ethylene propylene, and mixtures thereof), and mixtures thereof, and has an outer diameter in the range of 300 to 3000 μm, or 500 to 1500 μm, and a wall thickness in the range of 5 to 150 μm, or 20 to 100 μm.

The outer insulation has at least one first opening near the distal end of the cable. The at least one first opening is not particularly limited in shape as long as the opening allows for connecting a ring electrode through the opening to a material beneath the outer insulation via the bendable bridging element. For example, the at least one first opening can be circular, oval or rectangular in shape. In one embodiment, the first opening fully covers the second opening of the insulation layer of an insulated conductor of a conducting channel. In one embodiment, the outer isolation has two or more first openings.

The first opening, and in one embodiment each of the first openings in the case of more than one first opening, may be surrounded by a circumferential recess. A "circumferential recess" is a circumferential part of the cable, in which the outer insulation has a lower wall thickness compared to other parts of the outer insulation. Thus, the outer insulation of the cable is not fully removed for creating a circumferential recess in the cable. The circumferential recess may be created by laser ablation or cutting, in one embodiment laser ablation.

The circumferential recess can have a wall thickness of outer insulation in the range of 2 to 100 μm.

According to one embodiment, the first opening is surrounded by a circumferential recess. The circumferential recess can have a length and/or depth which is adjusted to the length and/or wall thickness of the ring electrodes. Thus, the circumferential recess can form a pocket into which the ring electrode can be embedded. Thereby, an isodiametric transition from the outer surface of the ring electrode to the surface of the outer insulation of the cable can be formed. Furthermore, the attached ring electrode does not pressure the remaining outer insulation of the cable of the first opening or the insulated conductors beneath the outer insulation since the dimensions of the circumferential recess can be fitted to the dimensions of the ring electrode. Of course, each ring electrode being present on the inventive lead may be, and in one embodiment are, attached to the cable in this way.

According to one embodiment, the at least one first opening, and in one embodiment each first opening, is surrounded by a circumferential recess of the outer insulation, wherein the at least one ring electrode, and in one embodiment each ring electrode, is embedded into the circumferential recess of one of the at least one first opening, and each one of the ring electrode(s) is isodiametric to the outer diameter of the cable.

According to one embodiment, the at least one first opening, and in one embodiment each first opening, is surrounded by a circumferential recess of the outer insulation, wherein the depth of the circumferential recess is essentially identical to the wall thickness of the at least one ring electrode. According to one embodiment, the at least one first opening, and in one embodiment each first opening, is surrounded by a circumferential recess of the outer insulation, wherein the length of the circumferential recess is essentially identical to the length of one of the at least one ring electrode.

According to one embodiment the at least first opening, in one embodiment each one of the at least one first openings, is/are surrounded by a circumferential recess of the outer insulation, wherein the depth of the circumferential recess is essentially identical to the wall thickness of one of the at least one ring electrode, and the length of the circumferential recess is essentially identical to the length of the at least one ring electrode.

According to one embodiment, the at least one first opening, in one embodiment each of the first openings, is/are surrounded by a circumferential recess of the outer insulation, wherein the depth of the circumferential recess is essentially identical to the wall thickness of the at least one ring electrode, in one embodiment of all ring electrodes, and the length of the circumferential recess is essentially identical to the length of the at least one ring electrode, in one embodiment of all ring electrodes, and wherein the at least one ring electrode is embedded into the circumferential recess of the at least one first opening, in one embodiment of all ring electrodes are separately embedded into one of the circumferential recesses.

According to one embodiment, the at least one first opening, in one embodiment each one of the first openings, is surrounded by a circumferential recess of the outer insulation, wherein the depth of the circumferential recess deviates a maximum of 20%, 10%, or 5%, from the wall thickness of one of the at least one ring electrode, and the length of the circumferential recess deviates a maximum of 20%, 10%, or 5%, from the length of the at least one ring electrode, and wherein the at least one ring electrode is embedded into the circumferential recess of the at least one first opening, in one embodiment all ring electrodes are separately embedded into the circumferential recess of one of the first openings.

According to another embodiment, each one of the at least one first opening is surrounded by a circumferential recess of the outer insulation, wherein the dimensions of the circumferential recess are adjusted to the dimensions of the ring electrodes to form pockets in the cable for the ring electrodes.

The cable comprises an inner lumen, wherein the inner lumen is arranged coaxially to the outer insulation and extends in a longitudinal direction from a proximal end to the distal end of the cable. Thus, in a radial cross section of the cable, the inner lumen is located essentially on the axis of the cable in its center.

The inner lumen has in one embodiment the dimensions of a stylet, i.e. a slender medical probe or device for implanting the lead, may be positioned and/or inserted into the lumen of the lead. In one embodiment, the inner lumen has a diameter in the range of 10 to 1000 μm, in the range of 50 to 500 μm, or in the range of 200 to 400 μm. For example, the diameter of the lumen may be about 350 μm.

The inner lumen may correspond to a hollow strand, which is only formed by the boundaries of the at least one conducting channel, which is arranged between the outer insulation and the inner lumen of the cable. Hence, in one embodiment, the inner lumen is formed by the at least one conducting channel which extends in a longitudinal direction from a proximal end to a distal end of the cable. For example, the at least one conducting channel may be helically wound to form the inner lumen of the cable. In one embodiment, the cable does not contain an inner tube which forms the inner lumen of the cable.

It is however preferred that the inner lumen of the cable is formed by an inner structure, in one embodiment an inner tube, or an inner polymer tube. The inner tube may be seen as a support structure between the at least one conducting channel which is arranged between the outer insulation and the inner lumen of the cable. The inner tube can provide the cable with an improved stability. The inner tube can comprise or consist of a flat metal band, which is braided. In one embodiment, the flat metal band is coated with a polymer film, like for example Pebax®.

The inner tube can have specific dimensions. The inner tube may have an outer diameter in the range of 10 to 1000 μm, in the range of 50 to 500 μm, or in the range of 200 to 400 μm. According to an exemplary embodiment, the outer diameter of the inner tube is about 350 μm and the inner diameter of the inner tube is about 250 μm. The inner tube may have a wall thickness in the range of 2 to 200 μm, 10 to 100 μm, or 20 to 80 μm. According to one embodiment, the inner tube has an outer diameter in the range of 50 to 500 μm, or in the range of 200 to 400 μm, and a wall thickness in the range of 10 to 100 μm, or 20 to 80 μm.

The inner polymer tube in one embodiment comprises a polymer selected from the group of silicones, polyolefins (e.g. polyethylene), polyurethanes, polyimides, polyamides, polyaryletherketone (e.g. polyether ether ketone), fluorinated polymers (e.g. selected from the group of ethylene tetrafluorethylene, polytetrafluorethylene, perfluoroalkoxy alkanes, polyvinylidene fluorides, fluorinated ethylene propylene, and mixtures thereof), and mixtures thereof. According to one embodiment, the inner polymer tube comprises a polymer selected from the group of silicones, polyolefins (e.g. polyethylene), polyurethanes, polyimides, polyamides, polyaryletherketone (e.g. polyether ether ketone), fluorinated polymers (e.g. selected from the group of ethylene tetrafluorethylene, polytetrafluorethylene, perfluoroalkoxy alkanes, polyvinylidene fluorides, fluorinated ethylene propylene, and mixtures thereof), and mixtures thereof, and has an outer diameter in the range of 50 to 500 μm, or in the range of 200 to 400 μm, and a wall thickness in the range of 10 to 100 μm, or 20 to 80 μm.

The cable comprises at least one conducting channel. For example, the cable may have between one and eighteen conducting channels. The at least one conducting channel is arranged between the outer insulation and the inner lumen of the cable. The at least one conducting channel is in electrical contact/communication with the at least one ring electrode near the distal end of the cable.

In one embodiment, the cable comprises at least four conducting channels (e.g. between four and eighteen conducting channels). According to one embodiment, the cable comprises four conducting channels. According to another embodiment, the cable comprises six conducting channels.

Each one of the at least one conducting channel is formed by at least one insulated conductor. The at least one insulated conductor is in one embodiment helically wound around the inner lumen of the cable. In case the inner lumen is formed by an inner tube, the at least one insulated conductor is in one embodiment helically wound around the inner tube of the cable.

The at least one insulated conductor of one the at least one conducting channel comprises a conductor and an insulation layer.

The conductor may be a single conductor or a multitude of single conductors. In one embodiment, the conductor is a metal wire or a multitude of metal wires, the plurality of metal wires being wound or coiled into a bundle of metal wires. The metal wire or bundle of metal wires may have a diameter in the range of 5 to 250 μm, or in the range of 10 to 120 μm. For example, the conductor (e.g. metal wire or bundle of metal wires) may have a diameter of about 85 μm.

The conductor in one embodiment comprises a metal selected from the group consisting of platinum, iridium, tantalum, palladium, titanium, iron, gold, molybdenum, niob, tungsten, nickel, chromium, cobalt, stainless steel, nitinol, alloys of each one of these metals, and composite materials of each one of these metals. Suitable as a conductor is stainless steel, for example, stainless steel AISI 316L, stainless steel AISI 301 or stainless steel AISI 304. Suitable as a conductor are platinum and platinum alloys, for example, Pt/Ir 10 or Pt/Ir 20. Suitable as conductor are nickel cobalt alloys such as MP35N.

The conductor may also be coated or plated with a coating (e.g. platinum) for increasing corrosion resistance. For example, the conductor may be a Pt-plated MP35N conductor or a Pt-plated tungsten-based conductor.

The insulation layer comprises a second opening, which is aligned with the at least one first opening. Thereby, the at least one first and the at least one second opening form one aligned first and second opening. This can be understood in that the insulation layer of the at least one insulated conductor comprises a second opening, which is aligned with a first opening A of the outer insulation, and the insulation layer of the at least one insulated conductor of a second conducting channel of the at least two conducting channels comprises a second opening, which is aligned with a first opening B of the outer insulation. The more ring electrodes the cable or lead has, the more first and second openings there will be, and therefore the more aligned first and second openings there will be in the cable or lead. The number of aligned first and second openings is determined by the number of ring electrodes as will be understood by a skilled person.

As defined above, the size and shape of the second opening is selected in a way that the part of the insulation layer of the insulated conductor, which is in contact with the insulation layer of an insulated conductor of another conducting channel, remains intact. Thus, the remaining insulation layer of the insulated conductor, which e.g. points radially inwards to the inner lumen or points towards insulated conductor(s) of another conducting channel is intact and functional. Thereby, the dielectric strength/resistance against electrical short circuits is increased. This is one important finding by the inventors.

According to one embodiment, the size of the second opening(s) in the insulation layer of the insulated conductor, as seen in a cross section, does not exceed 60%, 50%, or 40%, of the perimeter of the insulated conductor.

The insulation layer of the at least one conductor in one embodiment comprises, in one embodiment consists of, a polymer selected from the group consisting of polyolefins (e.g. polyethylene), polyurethanes, polyimides, polyamides, polyaryletherketone (e.g. polyether ether ketone), fluorinated polymers (e.g. selected from the group of ethylene tetrafluorethylene, polytetrafluorethylene, perfluoroalkoxy alkanes, polyvinylidene fluorides, fluorinated ethylene propylene, and mixtures thereof), and mixtures thereof.

In one embodiment, the insulation layer has a thickness in the range of 3 to 150 μm, or in the range of 5 to 40 μm. For example, the insulation layer may have a thickness of about 15 μm.

The at least one conducting channel is formed by at least one insulated conductor. The number of insulated conductors which form one conducting channel can depend on how many conducting channels the cable or lead shall have, and on how stable the connection of the ring electrode to the conductor of the conducting channel shall be.

For example, one conducting channel may be formed by one insulated conductor. This can have the advantage that the cable may include a high number of conducting channels (e.g. 6, 8, 10, 12, or 18), since the single insulated conductor per conducting channels which is arranged between the outer insulation and the inner lumen occupies comparatively little space. Thus, according to one embodiment, the at least one conducting channel is formed by one insulated conductor.

On the other hand, one conducting channel may be formed by two or more insulated conductors. In case one conducting channel is formed by two or more insulated conductors the second opening in the insulation layer of each one of the insulated conductors is at the same position of the cable, so to allow an alignment of all second openings of the insulation layers of the insulated conductors with one first opening of the outer insulation of the cable. This can have the advantage that the contact stability of one ring electrode to the conductors of one conducting channel is higher, since there is a larger contact area of conductor available for effecting the connection to the ring electrode. Thus, according to another embodiment, each one of the at least one conducting channel(s) is formed by two or more insulated conductors (e.g. two, three, four or five insulated conductors). According to one embodiment, each one of the at least one conducting channel(s) is formed by two or more insulated conductors, which are arranged adjacent to each other, wherein the second openings of the insulation layers of the insulated conductors are at the same position in the cable.

According to one embodiment, the at least one conducting channel, and in one embodiment each conducting channel, is formed by two or more insulated conductors, which are arranged adjacent to each other, wherein the second openings of the insulation layers of the two or more insulated conductors of the at least one conducting channel, in one embodiment each conducting channel, is aligned with the at least one first opening, and wherein the at least one ring electrode is selectively connected to the conductors of the two or more insulated conductors.

The lead of one embodiment comprises at least one ring electrode.

The at least one ring electrode, in one embodiment all ring electrodes, in one embodiment comprises a metal selected from the group consisting of platinum, iridium, tantalum, palladium, titanium, iron, gold, molybdenum, niob, tungsten, nickel, chromium, cobalt, steel, nitinol, alloys of each one of these metals, and composite materials of each one of these metals. Suitable as a ring electrode is stainless steel, for example, stainless steel AISI 316L, stainless steel AISI 301 or stainless steel AISI 304. Suitable as a ring electrode is platinum and platinum alloys, for example, Pt/Ir 10 or Pt/Ir 20. Suitable as a ring electrode are nickel cobalt alloys such as MP35N.

The choice of metal for the ring electrode (and for the conductor) may depend on the use of the inventive lead. For example, if the inventive lead is to be used in a permanent medical device, the at least one ring electrode may comprise, in one embodiment consist of, platinum or a platinum iridium alloy. If the inventive lead is to be used in a temporary medical device e.g. in a test trial, the at least one ring electrode may comprise, in one embodiment consist of, stainless steel. However, it is to be understood that the application of the lead is not limited by the use of a specific metal.

The at least one ring electrode, in one embodiment all ring electrodes, may comprise a coating. Suitable coatings are metal nitrides such as TiN, metal oxides such as $IrO_2$, conductive polymers or combinations thereof. The surface of the at least one ring electrode may also be surface-structured, e.g. laser-structured.

The at least one ring electrode, in one embodiment all ring electrodes, may has an outer diameter in the range of 200 to 5000 μm, or in the range of 300 to 3000 μm, or in the range of 500 to 1500 μm. The at least one ring electrode, in one embodiment all ring electrodes, may has/have a wall thickness in the range of 10 to 200 μm, 10 to 100 μm, or 30 to 70 μm. Furthermore, the at least one ring electrode, in one embodiment all ring electrodes, may has/have a length in the range of 200 to 5000 μm, 300 to 3000 μm, or in the range of 500 to 1500 μm. According to one embodiment, each the at least one ring electrode, in one embodiment all ring electrodes, has an outer diameter in the range of 300 to 3000 μm, or in the range of 500 to 1500 μm, a wall thickness in the range of 10 to 100 μm, or 30 to 70 μm, and a length in the range of 300 to 3000 μm, or in the range of 500 to 1500 μm.

According to one embodiment, the at least one ring electrode, in one embodiment all ring electrodes, has an outer diameter in the range of 300 to 3000 μm, or in the range of 500 to 1500 μm, a wall thickness in the range of 10 to 100 μm, or 30 to 70 μm, and a length in the range of 300 to 3000 μm, or in the range of 500 to 1500 μm, and comprises a metal selected from the group consisting of platinum, iridium, tantalum, palladium, titanium, iron, gold, molybdenum, niob, tungsten, nickel, chromium, cobalt, steel, nitinol, alloys of each one of these metals, and composite materials of each one of these metals.

The at least one ring electrode surrounds the cable at a position of the aligned first and second openings of the cable, and the at least one ring electrode is selectively connected to the conductor of the at least one insulated conductor of the at least one conducting channel through the aligned first and second openings via the bendable bridging element.

As specified above, the number of conducting channels determines the minimum number of ring electrodes near the distal end of the cable. It is possible that one conducting channel is connected near the distal end of the cable to one ring electrode or to several ring electrodes (which are all on the same electrical potential) via a bendable bridging element. For example, it is possible that one conducting channel is connected to five ring electrodes near the distal end of the cable, each via a bendable bridging element.

According to one embodiment, the number of the ring electrodes near the distal end of the cable and the conducting channels is the same. Thus, it is preferred that, when the lead has six conducting channels, there are six ring electrodes near the distal end of the cable which are selectively connected to each one of the conducting channels, each via a bendable bridging element.

However, there may be applications of the inventive lead where it is advantageous that one or all of the conducting channels is connected to two or more ring electrodes near the distal end of the cable. In this embodiment, the number of ring electrodes near the distal end of the cable is higher than the number of conducting channels. According to one embodiment, one or each one conducting channel of the at least one conducting channel is selectively connected to two or more ring electrodes near the distal end of the cable.

The at least one ring electrode is electrical connected to the conductor of the at least one insulated conductor via a bendable, in one embodiment reversible bendable, bridging element, which is positioned between the conductor and the ring electrode. The bendable bridging element extends radially inwards from the ring electrode through the aligned first and second opening of the cable and is in electrical contact with the at least one conductor of the at least one conducting channel of the cable. The bendable bridging elements therefor facilitates the electrical contact formation between the ring electrode and the conducting channel and provides a more robust and reliable electrical contact between those two elements.

The bridging element is bendable and thus has a spatial shape that is more easily deformable than would be possible via the pure plastic properties of the material of the bridging element. The bridging element thus has a shape which is more easily deformable than, for example, a sphere, such as a particle, a cube or a solid or hollow cone made of the same material as the bridging element. The bendability of the bridging element thus goes beyond the intrinsic bendability of the bridging element material.

In one embodiment, the bridging element is at least bendable in the radial direction, that is, from the ring electrode inwardly in the direction of the longitudinal axis of the cable.

A bendable bridging element has the advantage that it can compensate for production variations and can be used for a greater variety of spatial dimensions of the further components of the lead, such as different diameters of ring electrodes or cables and/or different thicknesses of the outer insulation.

Furthermore, a bendable bridging element facilitates the formation of the contact, in particular the electrical contact, between the ring electrode and the conductor. Non-bendable bridging elements, on the other hand, would have to be more precisely matched to the spatial dimensions of the lead, such as the thickness of the outer insulation and/or the thickness of the ring electrode, in order to ensure reliable electrical contact between the ring electrode and the conductor.

The bridging element is in one embodiment connected to the conductor by a first weld, preferable a first laser weld, and to the ring electrode by a second weld, in one embodiment a second laser weld.

In one embodiment, the bendable bridging element is a mesh. A mesh is a material distinguished by connected and crossing strands.

In order to allow a good bendability and therefor a reliable electrical connection between the conductor and the ring electrode, the mesh can have a strand thickness between 10 μm to 50 μm and a mesh width between 20 μm and 100 μm.

In one embodiment, the mesh as a mesh diameter which corresponds to the diameter of the first opening.

In one embodiment, the bendable bridging element is a wire extending essentially parallel to a longitudinal axis of the lead.

In one embodiment, the wire has a wire diameter in the range of 50 μm to 1000 μm. In one embodiment, the length of the wire is in the range of 200 μm and 1500 μm, or 500 μm and 1000 μm.

In one embodiment, the wire has a bend along the longitudinal axis of the wire, i.e. it is not straight, which is at least partially bent back when the ring electrode is applied to the cable. This facilitates the formation of a reliable electrical contact between the ring electrode and the conductor.

In one embodiment, the bendable bridging element is a metal ribbon or a metal wire extending radially outward from a center of the lead at least in portion thereof. This means that at least a part of the ribbon or wire extends outwardly, while another part or the remaining part of the ribbon or wire is in contact with the conductor and extends, for example, substantially parallel to the longitudinal axis of the cable. The radially outwardly extending part of the ribbon or wire may be fully or at least partially in electrical contact with the ring electrode.

In one embodiment, the ring electrode has an indentation through which the radially outwardly extending portion of the ribbon or wire extends. This simplifies the establishment of electrical contact between bridging elements and ring electrode. For example, the part of the ribbon or wire that extends through the indentation can be welded to it, in particular by using a laser.

In one embodiment, the ribbon or wire has a diameter in the range of 50 μm to 1000 μm. In one embodiment, the length of the ribbon or wire is in the range of 200 μm and 1500 μm, or 500 μm and 1000 μm.

In one embodiment, the bendable bridging element is a spring element. A spring element is an especially reversible, elastic object that stores mechanical energy.

In one embodiment, the spring element can be bent from the direction of the ring electrode in the direction of the conductor. A spring element is easily bendable, so that larger thickness variations can easily be compensated and a wide range of leads of different component groups can be produced with the same spring element. This facilitates the manufacture of the lead and, in particular in the event of production fluctuations due to variances in thicknesses various parts, simplifies the provision of a reliable electrical connection between the ring electrode and the conductor.

The spring element can be designed in different ways.

In one embodiment, the spring element is a leaf spring. A leaf spring has a simple design and thus permits comparatively inexpensive production of the lead. In one embodiment, one end of the leaf spring is connected to the ring electrode und the other end of the leaf spring is connected to the conductor(s).

The leaf spring can have a height in the range of 50 μm and 1000 μm and a width in the range of 50 μm and 500 μm.

In one embodiment, the leaf spring is equipped with a stopper element, like for example a protrusion, which is arranged at the end of the leaf spring facing away from the at least one conducting channel. The end of the leaf spring with the stopper element is connected to the ring electrode.

In one embodiment, if the leaf spring comprises a stopper element, the ring electrode comprises an indentation which can be engaged with the stopper element. This facilitates the assembly of the lead. The stopper element is in one embodiment welded to the indentation, in one embodiment by using a laser.

In one embodiment, the spring element is a coil spring. A coil spring has a simple design and thus permits comparatively inexpensive production of the lead. In one embodiment, one end of the coil spring is connected to the ring electrode und the other end of the coil spring is connected to the conductor(s).

The coil spring can have a different number of full or only partial coils. For example, the coil spring may have only one whole turn and one half turn. In one embodiment, the spring has 1 to 10 coils.

In one embodiment, the thickness of the wire from which the coil spring is made is in the range of 50 μm and 200 μm. In one embodiment, the axial extent of the coil spring from one end of the coil spring to the opposite end of the coil spring is in the range of 50 μm and 1000 μm and a width in the range of 50 μm and 500 μm.

In one embodiment, the bendable bridging element comprises a metal selected from the group consisting of platinum, iridium, tantalum, palladium, titanium, iron, gold, molybdenum, niob, tungsten, nickel chromium, cobalt, steel, nitinol, alloys of each one of these metals, and composite materials of each one of these metals. Suitable as a bendable bridging element is stainless steel, for example, stainless steel AISI 316L, stainless steel AISI 301 or stainless steel AISI 304. Suitable as a bendable bridging element are platinum and platinum alloys, for example, Pt/Ir 10 or Pt/Ir 20. Suitable as bendable bridging element are nickel cobalt alloys such as MP35N.

There are different options how to connect the ring electrode to the bridging element.

It is possible that the ring electrode comprises a protrusion (in one embodiment an electrode cup) which extends radially inwards from the ring electrode. In such case, the ring electrode may be connected to the bridging element via its protrusion (in one embodiment an electrode cup). An "electrode cup" is a protrusion which extends radially inwards from the wall of the ring electrode, which is obtainable by pressing the wall of the electrode inwardly (e.g. with a pin). The protrusion, in one embodiment the electrode cup, may have a width in the range of 50 to 400 μm (e.g. about 200 μm) and depth, as measured from the outer diameter of the ring electrode, in the range of 75 to 300 μm (e.g. about 130 μm).

In case the conductor to which the ring electrode is attached via the bendable bridging element is a multitude of metal wires (e.g. a coil or bundle of metal wires), the metal wires serving as contact area for the bridging element may be welded together to improve the connection between the conductor and the bridging element. Thus, according to one embodiment, the conductor of the at least one insulated conductor is a multitude of metal wires (e.g. a coil or bundle of metal wires), wherein the multitude of metal wires are welded together at the contact area for the bridging element.

The lead according to the present embodiment may be a unipolar lead, a bipolar lead or a multipolar lead. It is preferred that the lead is a multipolar lead. The multipolar lead is in one embodiment a lead with at least four conducting channels, e.g. from four to eighteen conducting channels. In such case, the lead comprises a cable including at least four conducting channels, e.g. from four to eighteen conducting channels.

According to one embodiment, the lead comprises six conducting channels.

The lead according to one embodiment comprises at least one proximal ring electrode near the proximal end of the cable, wherein the at least on proximal ring electrode is in electrical communication with the at least one ring electrode near the distal end of the cable. The number of proximal ring electrodes may be determined by the number of ring electrodes near the distal end of the cable. The at least one proximal ring electrode is in one embodiment designed and attached to the cable the same way as the at least one distal ring electrode. According to one embodiment, the lead comprises the same number of ring electrodes near the proximal end of the cable as it comprises ring electrodes near the distal end of the cable.

According to one embodiment, the lead comprises four ring electrodes near the distal end of the cable and four ring electrodes near the proximal end of the cable, wherein each one of the four ring electrodes near the proximal end of the cable is in electrical communication with one of the four electrodes near the distal end of the cable via one of four conducting channels of the lead. According to another embodiment, the lead comprises six ring electrodes near the distal end of the cable and six ring electrodes near the proximal end of the cable, wherein each one of the six ring electrodes near the proximal end of the cable is in electrical communication with one of the six ring electrodes near the distal end of the cable via one of six conducting channels of the lead.

If the lead comprises more than one ring electrode near the distal end of the cable and, if any, more than one ring electrode near the proximal end of the cable, the ring electrodes near the proximal and/or distal end of the cable may be positioned with a specific spacing to each other. The spacing of the ring electrodes can be selected and adjusted by the skilled person in view of the application of the lead, and in one embodiment in view of its medical application. According to one embodiment, the ring electrodes near the distal end of the cable are positioned with a spacing in the range of from 0.25 to 10 mm, in the range of from 0.5 to 6 mm, or in the range of from 1 to 4 mm. According to one embodiment, the ring electrodes near the proximal end of the cable are positioned with a spacing in the range of from 0.25 to 10 mm, in the range of from 0.5 to 6 mm, or in the range of from 1 to 4 mm. According to one embodiment, the ring electrodes near the proximal end of the cable are positioned with a spacing in the range of from 0.25 to 10 mm, in the range of from 0.5 to 6 mm, or in the range of from 1 to 4 mm, and the ring electrodes near the proximal end of the cable are positioned with a spacing in the range of from 0.25 to 10 mm, in the range of from 0.5 to 6 mm, or in the range of from 1 to 4 mm. The spacing between each one of the ring electrodes near one end of the cable may be the same or different, and in one embodiment is different.

The length of the lead may depend on the application of the lead, in one embodiment its medical application, and can be adjusted according to the needs of a skilled person. The lead in one embodiment has a length in the range of 50 to 5000 mm, 100 to 2000 mm, or 200 to 1000 mm. In an exemplary embodiment, the cable has a length of about 500 mm.

Furthermore, the lead may comprise one or more fixing elements at the distal end of the cable. The fixing elements of the lead may help to fix the lead for its medical application. For example, the lead may comprise barbs as fixing elements. The barbs are in one embodiment positioned on the outer surface of the outer insulation. The barbs may also be a part of the outer insulation of the cable. It is also possible that the lead comprises a spiral as a fixing element. The spiral is in one embodiment positioned at the distal end of the cable, and may have the form of a helix shaped polymer tip.

The lead of the present embodiment is useful for a medical device. The medical device may be a permanent medical device or a temporary medical device (e.g. for a medical trial). The medical device may be a pulse generator.

The lead of the present embodiment is in one embodiment used in a medical device for neuro modulation and/or neuro stimulation. For example, the inventive lead may be used in a device for neuro modulation and/or neuro stimulation if the spinal cord, the sacral nerve, peripheral nerves, gastric stimulation, face stimulation, pelvic floor pacemaker, lung pacing, and the like.

In another aspect of the present embodiment, a medical device is provided. The medical device comprises the lead according to one embodiment. The medical device may be a pulse generator. The medical device is in one embodiment used for neuro modulation and/or neuro stimulation. For example, medical device is used for neuro modulation and/or neuro stimulation if the spinal cord, the sacral nerve, peripheral nerves, gastric stimulation, face stimulation, pelvic floor pacemaker, lung pacing, and the like.

According to one embodiment, the medical device is a permanent medical device. According to another embodiment, the medical device is a temporary medical device (e.g. for a medical trial).

The Process for Preparing the Bi- or Multipolar Lead

Another aspect of one embodiment refers to the provision of a process for preparing a lead, in one embodiment a bi- or multipolar lead, in one embodiment a bi- or multipolar lead. The process comprises the steps of:

a) providing a cable including
   an outer insulation,
   an inner lumen,
   wherein the inner lumen is arranged coaxially to the outer insulation and extends in a longitudinal direction from a proximal end to a distal end of the cable,
   at least one conducting channel,
   wherein the at least one conducting channel is arranged between the outer insulation and the inner lumen of the cable,
   wherein the at least one conducting channel is formed by at least one insulated conductor including a conductor and an insulation layer;
b) providing at least one ring electrode;
c) providing at least one bendable bridging element;
d) removing parts of the outer insulation near the distal end of the cable to create at least one first opening;
e) removing parts of the insulation layer of the at least one insulated conductor beneath the at least one first opening to create at least one second opening,
   wherein the at least one second opening is aligned with the at least one first opening near the distal end of the cable;
f) positioning the at least one bridging element in the aligned first and second opening so that the bridging element is in electrical contact with the conductor;
g) attaching the bridging element to the conductor;
h) positioning the at least one ring electrode around the cable obtained in step g) at the position of the at least one aligned first and second opening;
i) attaching the at least one ring electrode to the bridging element thereby connecting the at least one ring electrode to the conductor.

It is to be understood that the process of this embodiment is a process for preparing the inventive lead as defined in detail in the foregoing section. Therefore, the embodiments of the inventive lead as defined in the foregoing section are also disclosed in combination with the process of the present embodiment and vice versa. A skilled person knows in view of the present specification of the inventive lead how to adapt the process of the embodiment to arrive at a specific embodiment of the inventive lead as defined in the foregoing section. For example, if a lead is to be prepared which has four or six proximal ring electrodes and four or six distal ring electrodes as described in the foregoing section, the skilled person knows how to adapt the single steps of the inventive process for preparing such a lead. According to one embodiment, the process is a process for preparing a multipolar lead including at least four conducting channels as defined herein, and at least four ring electrodes as defined herein near the distal end of the cable, and in one embodiment with at least four ring electrodes as defined herein near the proximal end of the cable.

In step a) of the process a cable is provided. The cable comprises an outer insulation; an inner lumen, wherein the inner lumen is arranged coaxially to the outer insulation and extends in a longitudinal direction from a proximal end to a distal end of the cable; at least one conducting channel, wherein the at least one insulated conductor is arranged between the outer insulation and the inner lumen of the cable, wherein the at least one conducting channel is formed by at least one insulated conductor including a conductor and an insulation layer.

Regarding the materials and the dimensions of the cable (i.e. the outer insulation, the inner lumen, the conducting channels, the conductors, the insulations layers), it is referred to the embodiments of the inventive lead as defined in the foregoing section. The same materials and dimensions of the cable are also suitable or preferred for the cable provided in step a).

The cable provided in step a) is in one embodiment manufactured by preparing the conducting channel(s) from at least one metal wire which is coated by an insulation layer. If the cable has more than one conducting channel, the conducting channels may be bundled or stranded. The conducting channel(s) is/are wrapped around the inner lumen or the inner tube forming the lumen. Then, the conducting channel(s) may be coated with an outer insulation e.g. by polymer extrusion or by drawing a polymer tube over the conducting channel(s). This way an "endless" cable can be produced on a spool, which is inexpensive, and easily processed.

Hence, according to one embodiment, the cable is provided in step a) by a process including the steps of: insulating a metal wire or a multitude of metal wires with an insulation layer to obtain at least one insulated conductor for each one of the at least two conducting channels; winding, in one embodiment in a helically way, the at least one insulated conductor of each one of the at least two conducting channels obtained in the previous step around an inner lumen (e.g. a hollow space or an inner tube); providing the at least one insulated conductor of each one of the at least two conducting channels obtained in the previous step with an outer insulation.

The processes for providing the cable of step a) are known to the skilled person and can be selected according to the desired embodiment of the cable.

Preferred exemplary embodiments of the cable provided in step a) are:

In step b) of the process, at least one ring electrode is provided.

Regarding the material of the at least one ring electrode (e.g. the metal, the coating, etc), it is referred to the embodiments of the inventive lead as defined in the foregoing section. The same materials of the at least one ring electrode are also suitable or preferred for the at least one ring electrode provided in step b).

The dimensions of the at least one ring electrode provided in step b) are comparable to those of the at least one ring electrode attached near the distal end of the cable of the inventive lead. However, it is to be understood that the diameter of the at least one ring electrode provided in step b) of the process has to be larger than the desired final diameter of the ring electrode on the inventive lead, to make up for the reduction of the ring electrodes diameter during the attaching step i). For example, if the desired final diameter of a ring electrode on the lead is 0.7 mm, then a ring electrode having a diameter of 0.83 mm may be provided in step b) of the process.

The at least one ring electrode provided in step b) may have an outer diameter in the range of 200 to 5500 μm, in the range of 300 to 3300 μm, or in the range of 500 to 1750 μm. The at least one ring electrode may have a wall thickness in the range of 10 to 200 μm, 10 to 150 μm, or 30 to 100 μm. Furthermore, the at least one ring electrode may have a length in the range of 200 to 5000 μm, 300 to 3000 μm, or in the range of 500 to 1500 μm. According to one embodiment, the at least one electrode has an outer diameter in the range of 300 to 3300 μm, or in the range of 500 to 1750 μm, a wall thickness in the range of 10 to 150 μm, or 30 to 100 μm, and a length in the range of 300 to 3000 μm, or in the range of 500 to 1500 μm. In one embodiment all ring electrodes of the lead comprise the same materials and have the same dimensions.

The at least one ring electrode provided in step b) may comprise a protrusion (in one embodiment an electrode cup) which extends radially inwards from the ring electrode. In one embodiment, the protrusion is an electrode cup, which is obtained by pressing in the wall of the ring electrode with a pin. The protrusion, in one embodiment the electrode cup, may have a width in the range of 50 to 400 μm (e.g. about 200 μm) and depth, as measured from the outer diameter of the ring electrode, in the range of 75 to 300 μm (e.g. about 130 μm).

Depending on the exact geometry of the at least one ring electrode (e.g. with or without protrusion), the at least one ring electrode may be provided in step b) in different ways.

According to one embodiment, the at least one ring electrode is provided in step b) by a deep drawing process including the steps of:

- forming a metal strip into a metal ring having a desired final geometry of the ring electrode by using a press and a deep-drawing die,
- further processing the metal ring by one or more steps selected from surface structuring, cutting, deburring, and polishing (e.g. magnetic vibratory grinding).

According to another embodiment, the at least one ring electrode is provided in step b) by a tube forming process including the steps of:

- providing a metal tube having a desired wall thickness and an outer diameter of the ring electrode,
- forming a protrusion in the wall of the metal tube, which extends radially inwards from the metal tube, in one embodiment by pressing in the wall of the ring electrode with a pin,
- further processing the intended metal tube by one or more steps selected from the group of surface structuring, cutting, deburring, and polishing (e.g. magnetic vibratory grinding).

The at least one ring electrode may comprise an indentation. The indentation may be provided in various way in the at least one ring electrode. For example, the indentation in the at least one ring electrode can be provided by using sawing, for example by using a circular saw, or by using cutting, for example by using a laser.

The processes for providing the at least one ring electrode of step b) are known to the skilled person and can be selected according to the desired at least one ring electrode of the inventive lead.

A preferred exemplary embodiment of the at least one ring electrode provided in step b) is:

A ring electrode having of a length of about 1400 μm, an inner diameter of about 750 μm, and an outer diameter of about 830 μm, and including an electrode cup having a width of about 200 μm and a depth, as measured from the outer diameter of the ring electrode, of about 130 μm.

In step c) of the process, at least one bendable bridging element is provided.

Regarding the type of the at least one bendable bridging element (mesh, wire, spring element, etc.) it is referred to the embodiments of the inventive lead as defined in the foregoing section. The same types of bendable bridging elements are also suitable or preferred for the at least one bendable bridging element provided in step c).

However, it is to be understood that the bendable bridging element provided in step c) of the process may have a slightly different shape then the bendable bridging element in the final lead. For example, the bendable bridging element may be provided in the form of a wire in a more bent shape than is present in the finished lead. Or, for example, the bendable bridging element in the form of a coil spring can be provided in a relaxed state, while the coil spring is in a compressed state in the finished lead.

Regarding the material of the at least one bendable bridging element (e.g. the metal, etc), it is referred to the embodiments of the inventive lead as defined in the foregoing section. The same materials of the at least one bendable bridging element are also suitable or preferred for the at least one bendable bridging element provided in step c).

The processes for providing the at least one bendable bridging element of step c) are known to the skilled person and can be selected according to the desired at least one bendable bridging element of the inventive lead.

In step d) and e) of the process, a part of the outer insulation near the distal end of the cable is removed to create at least one first opening, and a part of the insulation layer of the at least one insulated conductor of the at least one conducting channel beneath the at least one first opening is removed to create at least one second opening, wherein the at least one second opening is aligned with the at least one first opening. In view of the definition of the term "second opening" above, it is to be understood that the part of the insulation layer of the at least one insulated conductor of the at least one conducting channel which is removed in step e) is a part of the insulation layer which is not in contact with an insulation layer of an insulated conductor of another conducting channel. In one embodiment, the part of the insulation layer which is removed in step e) is a part on the top side of the insulated conductor.

Steps d) and e) can be carried out separately or together and are in one embodiment carried out simultaneously.

Step d) and/or step e) is in one embodiment carried out by laser ablation or by cutting. According to one embodiment, the steps d) and e) are carried out by laser ablation or by cutting.

In step d) of the process, parts of the outer insulation at the contact point are in one embodiment removed by laser ablation or mechanical cutting without damaging the insulation layer underneath the insulated conductor and the insulation layer of an insulated conductor of a neighboring conducting channel. The area of the outer insulation, which is removed in step d) at one contact point, may be larger than the area of the insulation layer removed in step e) at the same contact point. This can simplify taking out parts of the conductor of the insulated conductor in a subsequent step d2).

According to one embodiment, step d) further comprises removing circumferential parts of the outer insulation to create a circumferential recess, which surrounds the at least one first opening. The advantage of the circumferential recess is described in the foregoing section. In brief, a circumferential recess allows for attaching a ring electrode in an isodiametric way, which is a particularly desirable design, and ensures that the outer insulation around the first opening is not squeezed by the attached ring electrode.

According to one embodiment, step d) further comprises removing circumferential parts of the outer insulation to create a circumferential recess, which surrounds the at least one first opening, and wherein the ring electrode is embedded in step i) into the circumferential recesses of the cable in a way to form an isodiametric transition between the surface of the cable and the surface of the at least one ring electrode.

According to one embodiment, step d) further comprises removing circumferential parts of the outer insulation to create a circumferential recess, which surrounds the at least one first opening, wherein the depth of the circumferential recess deviates a maximum of 20%, 10%, or %, from the wall thickness of the ring electrode provided in step b), and wherein the length of the circumferential recess deviates a maximum of 20%, 10%, or 5%, from the length of the ring electrode provided in step b).

According to one embodiment, step d) further comprises removing circumferential parts of the outer insulation to create a circumferential recess, which surrounds the at least one first opening, wherein the depth of the circumferential recess is essentially identical to the wall thickness of the ring electrode provided in step b), and wherein the length of the circumferential recess is essentially identical to the length of the ring electrode provided in step b).

According to another embodiment, circumferential parts of the outer insulation are removed in step d) to create at least one circumferential first opening. According to one embodiment, circumferential parts of the outer insulation are removed in step d) to create at least one circumferential first opening, and wherein the at least one ring electrode is attached in step i) to the cable in a way to form an isodiametric transition between the surface of the cable and the surface of the at least one ring electrode. According to one embodiment, circumferential parts of the outer insulation are removed in step d) to create at least one circumferential first opening, and wherein step i) further comprises embedding the at least one ring electrode into the at least one circumferential first opening.

In step e) of the process, parts of the insulation layer of the at least one insulated conductor at the contact point are in one embodiment removed by laser ablation or mechanical cutting without damaging the insulation layer underneath the insulated conductor and the insulation layer of an insulated conductor of a neighboring conducting channel.

Furthermore, if the conductor of the at least one insulated conductor comprises a multitude of metal wires (e.g. a coil or bundle of metal wires), the multitude of metal wires which are exposed in the second opening obtained in step e) may be welded together to improve contact stability and/or the connecting process in subsequent steps. Thus, according to one embodiment, the conductor of the at least one insulated conductor the at least one conducting channel of the cable provided in step a) comprises a multitude of metal wires (e.g. a bundle of metal wires), and step e) comprises a step e2) of welding together the multitude of metal wires in the second opening.

In step f) of the process, the at least one bridging element is positioned in the aligned first and second opening so that the bendable bridging element is in electrical contact with the conductor. The positioning of the bridging element may be done by any suitable means known to the skilled person.

In step g) of the process, the positioned bridging element is attached to the conductor so that the bridging element is in electrical contact with the conductor. In one embodiment of the process, in step g) the bridging element is connected to the conductor by welding, by using laser welding.

After step g) of the process, the bridging element extends radially outward from the conductor through at least portions of the second opening, and in one embodiment at least portions of the first opening.

In step h) of the process, the at least one ring electrode is positioned around the cable obtained in step e) at the position of the at least two aligned first and second openings. In one embodiment, step h) establishes electrical contact between the ring electrode and the bridging element. The positioning of the ring electrode may be done by any suitable means known to the skilled person.

In step i) of the process, the at least one ring electrode is attached to the bridging element thereby selectively connecting the at least one ring electrode to the at least one conductor of the at least one insulated conductor of the at least one conducting channel through the aligned first and second openings.

According to one embodiment, the at least one ring electrode is attached in step i) by swaging. It is one advantage of the present embodiment that step i) may be carried out by swaging without the use of a welding step. This simplifies the inventive process compares to known processes. Thus, according to one embodiment, step i) does not contain a welding of the at least one ring electrode. It is however possible to attach the at least one ring electrode to the bridging element by welding, preferable by laser welding. Thus, according to another embodiment, the at least one ring electrode is attached in step i) by welding. According to another embodiment, the at least one ring electrode is attached in step i) by swaging and welding.

The process according to the present embodiment may comprise additional process steps of capping one end of the lead, adding fixing elements to the distal end of the lead (e.g. a spiral), cutting the outer insulation of the lead to form fixing elements (e.g. barbs), surface structuring (e.g. stamping) the at least one ring electrode, finishing the lead, and the like. Such processes are known to the skilled person and can be selected and adjusted according to the desired application of the lead, in one embodiment to the desired application in a medical device.

The features disclosed in the claims, the specification, and the drawings maybe essential for different embodiments of the claimed invention, both separately and in any combination with each other.

It is to be understood that the features of the various exemplary embodiments described herein may be combined with each other, unless specifically noted otherwise.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

The invention claimed is:

1. A lead for a medical device comprising:

a cable comprising:

an outer insulation having at least one first opening near a distal end of the cable; and an inner lumen;

wherein the inner lumen is arranged coaxially to the outer insulation and extends in a longitudinal direction from a proximal end to the distal end of the cable;

at least one conducting channel;

wherein the at least one conducting channel is arranged between the outer insulation and the inner lumen of the cable;

wherein the at least one conducting channel is formed by at least one insulated conductor comprising a conductor and an insulation layer, and wherein the insulation layer of the at least one insulated conductor comprises a second opening, which is aligned with the at least one first opening;

at least one ring electrode;

wherein the at least one ring electrode surrounds the cable at a position of the at least one aligned first and second opening of the cable; and wherein the at least one ring electrode is selectively connected to the conductor of the at least one insulated conductor via a bendable bridging element extending through the at least one aligned first and second opening; and wherein the bendable bridging element is one of a mesh, a leaf spring, and a wire having a longitudinal axis that extends essentially parallel to the longitudinal direction of the cable.

2. The lead according to claim 1, wherein the lead is a multipolar lead comprising:

a cable comprising an outer insulation having at least four first openings near a distal end of the cable;

an inner lumen;

wherein the inner lumen is arranged coaxially to the outer insulation and extends in a longitudinal direction from a proximal end to the distal end of the cable;

at least four conducting channels;

wherein the at least four conducting channels are arranged between the outer insulation and the inner lumen of the cable;

wherein each one of the at least four conducting channels is formed by at least one insulated conductor comprising a conductor and an insulation layer; and wherein the insulation layer of the at least one insulated conductor of each one of the at least four conducting channels comprises a second opening, which is aligned with one of the at least four first openings;

at least four ring electrodes;

wherein each one of the at least four ring electrodes surrounds the cable at a position of one of at least four aligned first and second openings of the cable; and wherein each one of the at least four ring electrodes is selectively connected to the conductor of the at least one insulated conductor via a bendable bridging element extending through each one of the at least four aligned first and second openings.

3. The lead according to claim 1, wherein the at least one conducting channel is formed by two or more insulated conductors, which are arranged adjacent to each other;

wherein each one of the two or more insulated conductors comprises at least one second opening and wherein the second openings of the insulation layers of the two or more insulated conductors of the at least one conducting channel are aligned with the at least one first opening; and wherein the at least one ring electrode is selectively connected to the conductors of the two or more insulated conductors via a bendable bridging element extending through the at least one aligned first and second openings.

4. The lead according to claim 1, wherein the bridging element is a metal ribbon or wire extending radially outward from a center of the lead in at least in portion thereof.

5. The lead according to claim 1, wherein the bridging element is a spring element.

6. The lead according to claim 1, wherein the bridging element is a leaf spring with a stopper element, which is arranged at an end of the leaf spring facing away from the at least one conducting channel.

7. The lead according to claim 1, wherein the bridging element is a coil spring.

8. The lead according to claim 1, wherein the bridging element comprises a metal selected from the group consisting of platinum, iridium, tantalum, palladium, titanium, iron, gold, molybdenum, niob, tungsten, nickel chromium, cobalt, steel, nitinol, alloys of each one of these metals, and composite materials of each one of these metals.

9. The lead according to claim 1, wherein the lead comprises the same number of ring electrodes near the proximal end of the cable as it comprises ring electrodes near the distal end of the cable, and wherein each one of the ring electrodes near the proximal end of the cable is in communication with one of the ring electrodes near the distal end of the cable via one conducting channel of the lead.

10. The lead according to claim 1, wherein the outer insulation of the cable has one or more of an outer diameter in the range of 200 to 5000 μm, and a wall thickness in the range of 2 to 300 μm.

11. The lead according to claim 1, wherein the inner lumen has a diameter in the range of 10 to 1000 μm.

12. The lead according to claim 1, wherein the inner lumen is formed by an inner tube.

13. The lead according to claim 1, wherein the conductor of the at least one insulated conductor of the at least two conducting channels comprises a metal selected from the group consisting of platinum, iridium, tantalum, palladium, titanium, iron, gold, molybdenum, niob, tungsten, nickel, chromium, cobalt, steel, nitinol, alloys of each one of these metals, and composite materials of each one of these metals.

14. The lead according to claim 1, wherein the at least two ring electrodes comprise a metal selected from the group consisting of platinum, iridium, tantalum, palladium, titanium, iron, gold, molybdenum, niob, tungsten, nickel, chromium, cobalt, steel, nitinol, alloys of each one of these metals, and composite materials of each one of these metals.

15. A process for preparing a lead, wherein the process comprises:

a) providing a cable comprising
an outer insulation,
an inner lumen,
wherein the inner lumen is arranged coaxially to the outer insulation and extends in a longitudinal direction from a proximal end to a distal end of the cable,
at least one conducting channel,
wherein the at least one conducting channel is arranged between the outer insulation and the inner lumen of the cable,
wherein the at least one conducting channel is formed by at least one insulated conductor comprising a conductor and an insulation layer;

b) providing at least one ring electrode;

c) providing at least one bendable bridging element;

d) removing parts of the outer insulation near the distal end of the cable to create at least one first opening;

e) removing parts of the insulation layer of the at least one insulated conductor beneath the at least one first opening to create at least one second opening,
wherein the at least one second opening is aligned with the at least one first opening near the distal end of the cable;

f) positioning the at least one bridging element in the aligned first and second opening so that the bridging element is in electrical contact with the conductor;

g) attaching the bridging element to the conductor;

h) positioning the at least one ring electrode around the cable obtained in step g) at the position of the at least one aligned first and second opening;

i) attaching the at least one ring electrode to the bridging element thereby connecting the at least one ring electrode to the conductor; and j) wherein the bendable bridging element is one of a mesh, a leaf spring, and a wire having a longitudinal axis that extends essentially parallel to the longitudinal direction of the cable.

16. The process according to claim 15, wherein steps d) and e) are carried out by laser ablation or by cutting.

17. The process according to claim 15, wherein the at least one ring electrodes is attached in step i) by swaging or by swaging and laser welding.

* * * * *